US012733994B2

(12) United States Patent
Balicki et al.

(10) Patent No.: US 12,733,994 B2
(45) Date of Patent: Sep. 15, 2026

(54) ELONGATED DEVICE TRACKING

(71) Applicant: KONINKLIJKE PHILIPS N.V., Eindhoven (NL)

(72) Inventors: Marcin Arkadiusz Balicki, Cambridge, MA (US); Alexandru Patriciu, Belmont, MA (US); Javad Fotouhi, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 19/138,171

(22) PCT Filed: Dec. 14, 2023

(86) PCT No.: PCT/EP2023/085736
§ 371 (c)(1),
(2) Date: Jun. 12, 2025

(87) PCT Pub. No.: WO2024/126639
PCT Pub. Date: Jun. 20, 2024

(65) Prior Publication Data
US 2026/0199023 A1 Jul. 16, 2026

Related U.S. Application Data

(60) Provisional application No. 63/433,030, filed on Dec. 16, 2022.

(30) Foreign Application Priority Data

Mar. 30, 2023 (EP) .................................... 23165401

(51) Int. Cl.
*A61B 34/00* (2016.01)
*A61B 34/20* (2016.01)
(Continued)

(52) U.S. Cl.
CPC .............. *A61B 34/20* (2016.02); *A61B 34/30* (2016.02); *A61B 90/37* (2016.02);
(Continued)

(58) Field of Classification Search
CPC ...................................................... A61B 34/20
See application file for complete search history.

(56) References Cited

U.S. PATENT DOCUMENTS

2008/0262473 A1 10/2008 Kornblau
2009/0192523 A1 7/2009 Larkin
(Continued)

FOREIGN PATENT DOCUMENTS

WO 2021240381 A1 12/2021

OTHER PUBLICATIONS

International Search Report and Written Opinion Dated Apr. 4, 2024 for International Application No. PCT/EP2023/085736 Filed Dec. 14, 2023.

*Primary Examiner* — Joseph M Santos Rodriguez

(57) ABSTRACT

A system for tracking coaxial elongated devices in anatomy includes a controller comprising a first interface and a second interface. The coaxial elongated devices comprise an outer elongated device and an inner elongated device driven by a motor. The first interface is configured to receive images including at least one of the outer elongated device or the coaxial inner elongated device. The second interface is configured to receive encoding data representative of the driving of the coaxial inner elongated device by the motor. The controller is configured to receive image including at least one of the outer elongated device, the coaxial inner elongated device being retracted within the outer elongated device; receive the encoding data; determine positions of the outer elongated device; and estimate locations of the coaxial inner elongated device retracted within the outer elongated
(Continued)

device based on the positions of the outer elongated device and the encoding data.

22 Claims, 6 Drawing Sheets

(51) Int. Cl.
*A61B 34/30* (2016.01)
*A61B 90/00* (2016.01)
(52) U.S. Cl.
CPC ................. *A61B 2034/2055* (2016.02); *A61B 2034/2059* (2016.02); *A61B 2034/301* (2016.02); *A61B 2090/376* (2016.02)

(56) References Cited

U.S. PATENT DOCUMENTS

| | | | |
|---|---|---|---|
| 2021/0100627 | A1 | 4/2021 | Soper |
| 2021/0177523 | A1 | 6/2021 | Ebrahimi |
| 2021/0369355 | A1 | 12/2021 | Masaki |

100

IMAGING DEVICE 101

DISPLAY 180

I/F 111

COMPUTER 110

120

ROBOT 130

MOTOR 140

ENCODER 145

I/F 112

CONTROLLER 150

MEMORY 151

PROCESSOR 152

381

481

581B

581A

ELONGATED DEVICE TRACKING

CROSS REFERENCE TO RELATED APPLICATIONS

This application is the U.S. National Phase application under 35 U.S.C. § 371 of International Application No. PCT/EP2023/085736 filed Dec. 14, 2023, which claims the benefit of U.S. Provisional Patent Application No. 63/433,030 filed Dec. 16, 2022 and European Patent Application Number 23165401.3 filed Mar. 30, 2023. These applications are hereby incorporated by reference herein.

BACKGROUND

In endovascular interventions, fluoroscopic images are used to independently manipulate coaxial endovascular devices. Coaxial endovascular devices include an inner device such as a guidewire and an outer device such as a catheter. The inner device may be retracted into and advanced from the outer device. The opacity of the catheter makes it challenging to observe the location of the tip of the guidewire when the tip of the guidewire is retracted inside the catheter. Moreover, this creates a cavity in the outer device where blood pools and can coagulate. Furthermore, when the guidewire is protracted, there is a risk of damage of the enclosing vessel.

The inability to know the location of the tip of the guidewire may be particularly problematic when a physician fails to notice that the guidewire is left retracted sufficiently to create a cavity in the outer device for a long time where blood pools and can coagulate. When the guidewire is again advanced, a clot may be embolized, and this is potentially life-threatening. In addition, during guidewire exchanges the guidewire may be advanced rapidly inside the outer device, and has the potential of advancing undesirably fast from the outer device and damaging the enclosing vessel. For example, a guidewire that is advanced undesirably fast and without knowledge of the location of the tip of the guidewire may perforate the endothelium.

SUMMARY

According to an aspect of the present disclosure, a system for tracking coaxial elongated devices in anatomy includes a controller comprising a first interface and a second interface. The coaxial elongated devices comprise an outer elongated device and an inner elongated device driven by a motor. The first interface is configured to receive images including at least one of the outer elongated device or the coaxial inner elongated device. The second interface is configured to receive encoding data representative of the driving of the coaxial inner elongated device by the motor. The controller is configured to receive image including at least one of the outer elongated device, the coaxial inner elongated device being retracted within the outer elongated device; receive the encoding data; determine positions of the outer elongated device; and estimate locations of the coaxial inner elongated device retracted within the outer elongated device based on the positions of the outer elongated device and the encoding data.

According to this aspect of the present disclosure, further optional embodiments are disclosed in claims 2 to 15.

According to another aspect of the present disclosure, a controller for tracking coaxial elongated devices in an anatomy includes a memory that stores instructions; a processor that executes the instructions; a first interface; and a second interface. The first interface is configured to receive images including an outer elongated device with a coaxial inner elongated device driven by the motor. The second interface is configured to receive encoding data corresponding to driving of the coaxial inner elongated device by a motor. When executed by the processor, the instructions cause the system to: receive the images including at least one of the outer elongated device and the coaxial inner elongated device; receive the encoding data; determine positions of the outer elongated device; and estimate locations of the coaxial inner elongated device retracted within the outer elongated device based on the positions of the outer elongated device and the encoding data.

According to this other aspect of the present disclosure, further optional embodiments are disclosed in claims 17 to 18.

According to another aspect of the present disclosure, a method for tracking coaxial elongated devices in an anatomy includes receiving, via a first interface, images including at least one of an outer elongated device or a coaxial inner elongated device driven by a motor; receiving, via a second interface, encoding data corresponding to driving of the coaxial inner elongated device by the motor; determining positions of the outer elongated device; and estimating locations of the coaxial inner elongated device retracted within the outer elongated device based on the positions of the outer elongated device and the encoding data.

According to this other aspect of the present disclosure, further optional embodiments are disclosed in claims 20 to 22.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
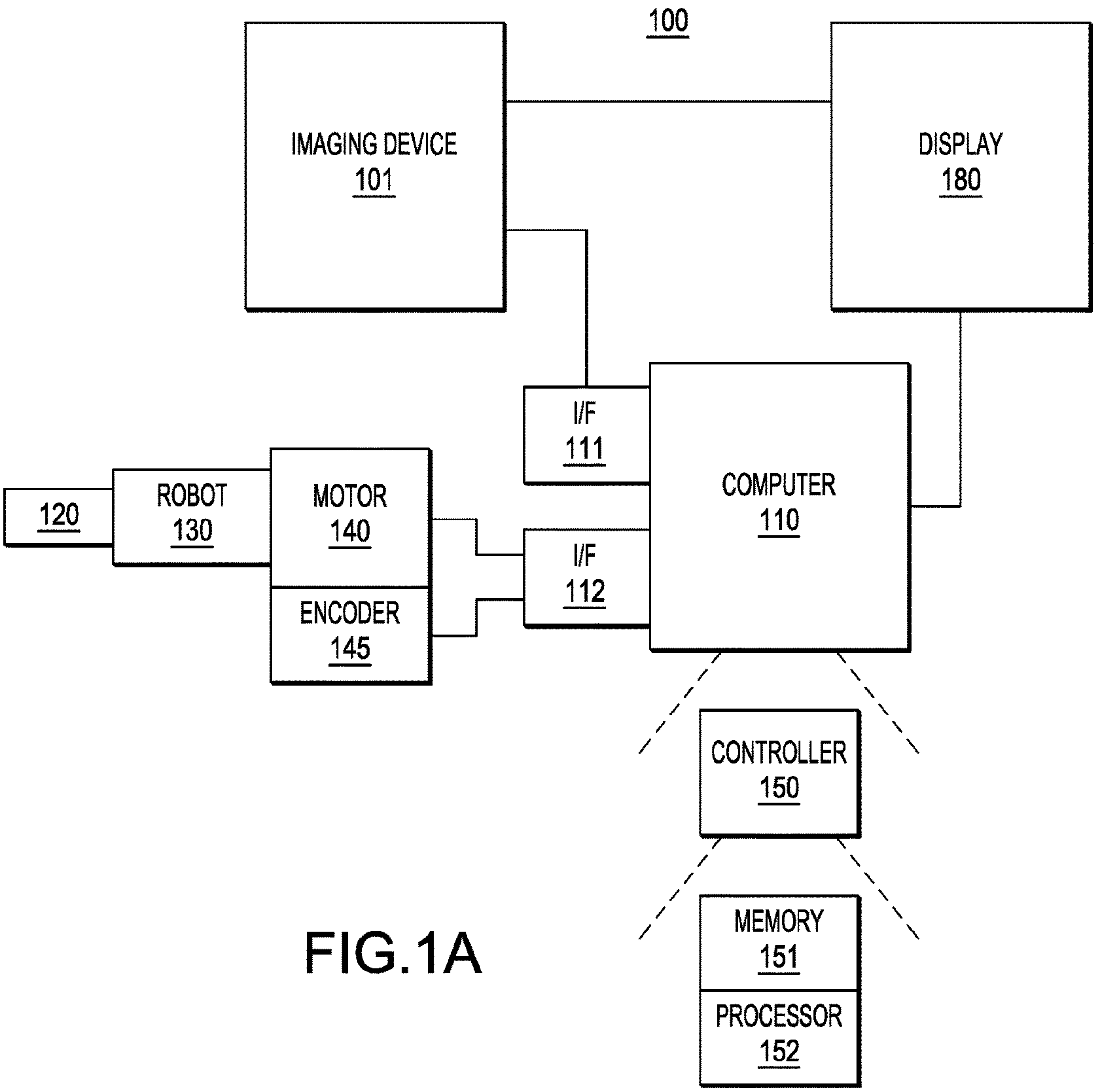
FIG. 1A illustrates a system for elongated device tracking, in accordance with a representative embodiment.

In the following detailed description, for the purposes of explanation and not limitation, representative embodiments disclosing specific details are set forth in order to provide a thorough understanding of embodiments according to the present teachings. However, other embodiments consistent with the present disclosure that depart from specific details disclosed herein remain within the scope of the appended claims. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. Definitions and explanations for terms herein are in addition to the technical and scientific meanings of the terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below.

As described herein, visual cues may be incorporated on a fluoroscopy image so that a physician may clearly monitor the location of the guidewire tip inside the catheter.

FIG. 1A illustrates a system 100 for elongated device tracking, in accordance with a representative embodiment.

The system 100 in FIG. 1A is a system for elongated device tracking and includes components that may be provided together or that may be distributed. The system 100 includes an imaging device 101, an elongated device 120, a robot 130, a motor 140, and a display 180. The robot 130 and the motor 140 may comprise separate elements or an integrated element or system. The computer 110 includes a first interface 111, a second interface 112 and a controller 150.

The controller 150 includes at least a memory 151 that stores instructions and a processor 152 that executes the instructions.

The imaging device 101 may comprise an X-ray device or system. The imaging device 101 may be configured to provide a two-dimensional X-ray image including the elongated device 120 including a tip of the elongated device.

Figure 6:
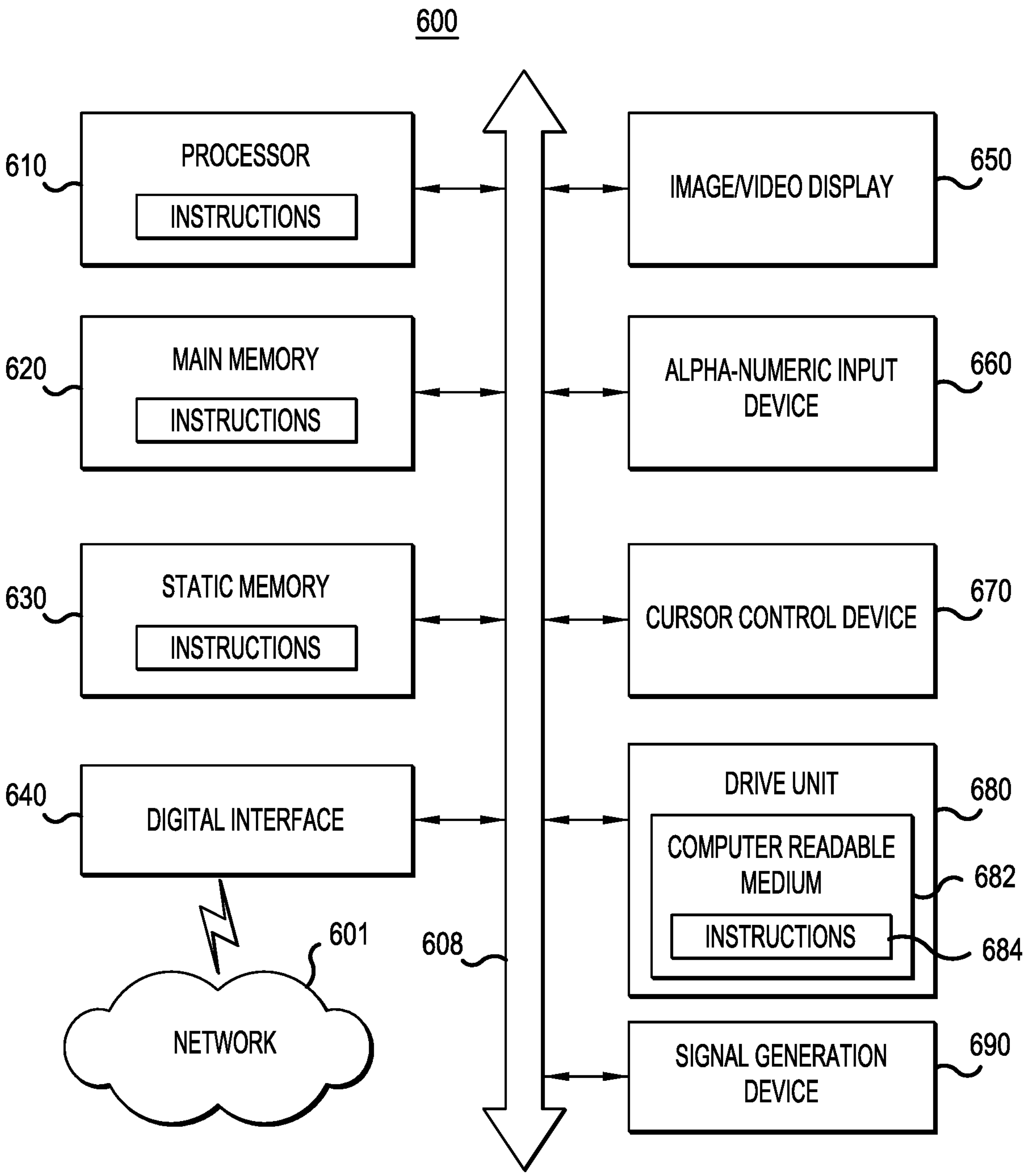
FIG. 6 illustrates a computer system, on which a method for elongated device tracking is implemented, in accordance with another representative embodiment.

The computer 110 may comprise a workstation, a laptop, a desktop, a specialized computer, or a virtual machine running on a local or remote cloud service. The computer 110 is used to control and/or coordinate operations of the imaging device 101, the motor 140, the robot 130 and the display 180. A computer that can be used to implement the computer 110 is depicted in FIG. 6, though a computer 110 may include more or fewer elements than depicted in FIG. 1 or FIG. 6. The computer 110 includes at least a first interface 111, a second interface 112 and the controller 150. The first interface 111 interfaces the computer 110 with the imaging device 101. The second interface 112 interfaces the computer 110 with the motor 140 and/or the encoder 145. Another interface (not shown or labelled) interfaces the computer 110 with the display 180. The first interface 141 and the second interface 142 may comprise ports, adapters and/or other types of appropriate hardware configured to accept cable inputs from cables connecting to the imaging device 101, the motor 140 and/or encoder 145, and display 180.

The controller 150 includes at least a memory 151 that stores instructions and a processor 152 that executes the instructions. In some embodiments, multiple different elements of the system 100 in FIG. 1 may include a controller such as the controller 150. The controller 150 may also include interfaces, such as a third interface, a fourth interface, a fifth interface and a sixth interface. One or more of the interfaces of the controller 150 may include ports, disk drives, wireless antennas, or other types of receiver circuitry that connect the controller 150 to other electronic elements of the computer 110 or outside of the computer 110. The controller 150 may be configured to receive via the first interface 111 images including image data of at least one of the outer elongated device, the inner elongated device being retracted within the outer elongated device. One or more of the interfaces of the computer 110 or specific to the controller 150 may also include user interfaces such as buttons, keys, a mouse, a microphone, a speaker, a display separate from the display 180, or other elements that users can use to interact with the computer 110 or specifically with the controller 150 such as to enter instructions and receive output.

In some embodiments, interfaces of the controller 150 may include a user interface used by a user to control the robot 130. A user interface may provide haptic feedback by vibrating when the guidewire crosses the alignment position with the catheter. In some embodiments, another element such as the robot 130 may vibrate when alignment approaches. In other embodiments, an interface on the robot 130 or the motor 140 may vibrate or illuminate when alignment is approached.

Audio feedback is added whenever the guidewire is retracted more than X amount into the catheter. For example 1 mm. The audio feedback could be a beep, a verbal mm readout, or other special effect sounds.

The memory 151 may store an association between encoding data from the encoder 145 and pixel position data along the catheter as the outer device of the elongated device 120. The processor 152 may assess the position of the tip of the guidewire as the inner device of the elongated device 120 along the outer device when the inner device is retracted by the motor 140. The processor 152 may further generate and send overlay information to the display 180 so as to overlay a (highlighted) indicator on the two-dimensional X-ray image. The overlaid indicator may be overlaid on the two-dimensional X-ray image along the outer device, at the assessed position of the tip of the inner device once the tip of the inner device is fully retracted within the outer device. The overlaid indicator is placed at a location on the two-dimensional X-ray image based on the encoding data from the encoder 145 and the stored association between the encoding data from the encoder 145 and the pixel position data along the catheter as the outer device of the elongated device 120.

The controller 150 may perform some of the operations described herein directly and may implement other operations described herein indirectly. For example, the controller 150 may indirectly control operations such as by generating and transmitting content to be displayed on the display 180. The controller 150 may be configured to provide display information such that the display 180 can show estimated locations of the inner elongated device superimposed on the outer elongated device. The controller 150 may directly control other operations such as logical operations performed by the processor 152 executing instructions from the memory 151 based on input received from electronic elements and/or users via the interfaces. Accordingly, the processes implemented by the controller 150 when the processor 152 executes instructions from the memory 151 may include steps not directly performed by the controller 150. In some embodiments, the controller 150 may perform operations by executing instructions received from the cloud, such as from a server in a data center.

The elongated device 120 may comprise an endovascular device, such as coaxial combination of two endovascular devices. In the descriptions herein, the elongated device 120 is primarily described in the context of a combination of a catheter as an outer device and a guidewire as an inner device. The motion of the guidewire as the inner device within the catheter as the outer device may be controlled by the robot 130 under the power of the motor 140. The controller 150 may be configured to control motion of at least one of the outer elongated device and the inner elongated device. In some embodiments, the controller 150 may automatically control velocity of the elongated device 120, such as by instructing the motor 140 to reduce power and/or the robot 130 to slow movement when the guidewire is inside the catheter as the guidewire approaches the alignment point while advancing.

The robot 130 may comprise a controllable device powered by the motor 140 and movable in one or more degrees of freedom. The robot 130 is configured to drive the elongated device 120 at least forward and backwards as one degree of freedom. The robot 130 may also be configured to rotate the elongated device 120 as a second degree of freedom. The robot 130 may also be configured to move the elongated device 120 vertically up and down as a third degree of freedom, and side to side as a fourth degree of freedom.

The motor 140 may comprise an electric motor, a linear motor, a precision stepper motor, or a servo motor ('servo'). In some embodiments, the robot 130 and the motor 140 may comprise an integrated unit referenced as either or both of a robot and/or a motor. The motor 140 is configured to drive the robot 130 to drive the elongated device 120 in the one or more degrees of freedom. A robotic system may comprise, for example, the motor 140 and the controller 150, or a combination of the robot 130 and the motor 140 along with the controller 150.

The motor 140 is also provided with an encoder 145 that tracks and encodes movement of the robot 130 and thus the elongated device 120 in the one or more degrees of freedom. The encoder 145 outputs encoded data reflecting the amount of movement of the robot 130 and thus the elongated device 120 in each degree of freedom.

The display 180 may be local to the controller 150 or may be remotely connected to the controller 150. The display 180 may be connected to the controller 150 via a local wired interface such as an Ethernet cable or via a local wireless interface such as a Wi-Fi connection. The display 180 may be interfaced with other user input devices by which users can input instructions, including mouses, keyboards, thumb wheels and so on. The display 180 may be a monitor such as a computer monitor, a display on a mobile device, an augmented reality display, a television, an electronic white-board, or another screen configured to display electronic imagery. The display 180 may also include one or more input interface(s) such as those noted above that may connect to other elements or components, as well as an interactive touch screen configured to display prompts to users and collect touch input from users. In some embodiments, the display 180 may display warnings, such as an arrow or text near the intersection of the catheter and the edge of a two-dimensional X-ray image when the guidewire is not in the current field of view. The controller 150 may be configured to calculate approximate distances in pixels from a tip of the outer elongated device to a tip of the inner elongated device. In some embodiments, the display 180 may display distance of the position of the tip of the guidewire relative to the tip of the catheter such as via a numerical display or a separate linear display or a color overlay of the section of the catheter that does not have the guidewire, i.e., the empty space between the tip of the catheter and the tip of the guidewire.

The controller 150 may also include interfaces, such as a first interface, a second interface, a third interface, and a fourth interface. One or more of the interfaces may include ports, disk drives, wireless antennas, or other types of receiver circuitry that connect the controller 150 to other electronic elements. One or more of the interfaces may also include user interfaces such as buttons, keys, a mouse, a microphone, a speaker, a display separate from the display 180, or other elements that users can use to interact with the controller 150 such as to enter instructions and receive output.

As set forth above, the system 100 may comprise a system for tracking coaxial elongated devices such as the elongated device 120. The coaxial elongated devices may comprise an outer elongated device and an inner elongated device driven by a motor such as the motor 140. The system 100 may comprise a computer with a controller such as the computer 110 with the controller 150. The computer may include a first interface such as the first interface 111 configured to receive images including image data of at least one of the outer elongated device or the coaxial inner elongated device; and a second interface such as the second interface 112 configured to receive encoding data representative of the driving of the coaxial inner elongated device by the motor. The controller of the system 100 is configured to: receive image including at least one of the outer elongated device, the coaxial inner elongated device being retracted within the outer elongated device; receive the encoding data; determine positions of the outer elongated device; and estimate locations of the coaxial inner elongated device retracted within the outer elongated device based on the positions of the outer elongated device and the encoding data.

Figure 1B:
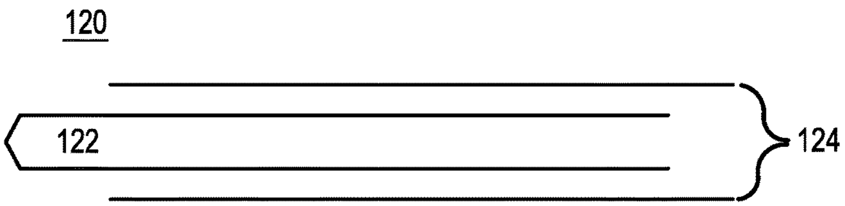
FIG. 1B illustrates an elongated device for elongated device tracking, in accordance with a representative embodiment.

FIG. 1B illustrates an elongated device for elongated device tracking, in accordance with a representative embodiment.

In FIG. 1B, an elongated device 120 is shown to include an outer elongated device 124 with an inner elongated device 122. The outer elongated device 124 may comprise a catheter and the inner elongated device 122 may comprise a guidewire.

Although not shown in FIG. 1B, an elongated device 120 may also be tracked without the encoder 145 in some embodiments. For example, external means of encoding the relative position between the guidewire and catheter may be used. In some embodiments, optical shape sensing may be used. In other embodiments, markers and cameras on the proximal section of the elongated device 120 may be used to track movement by the robot 130 and the motor 140.

Figure 2:
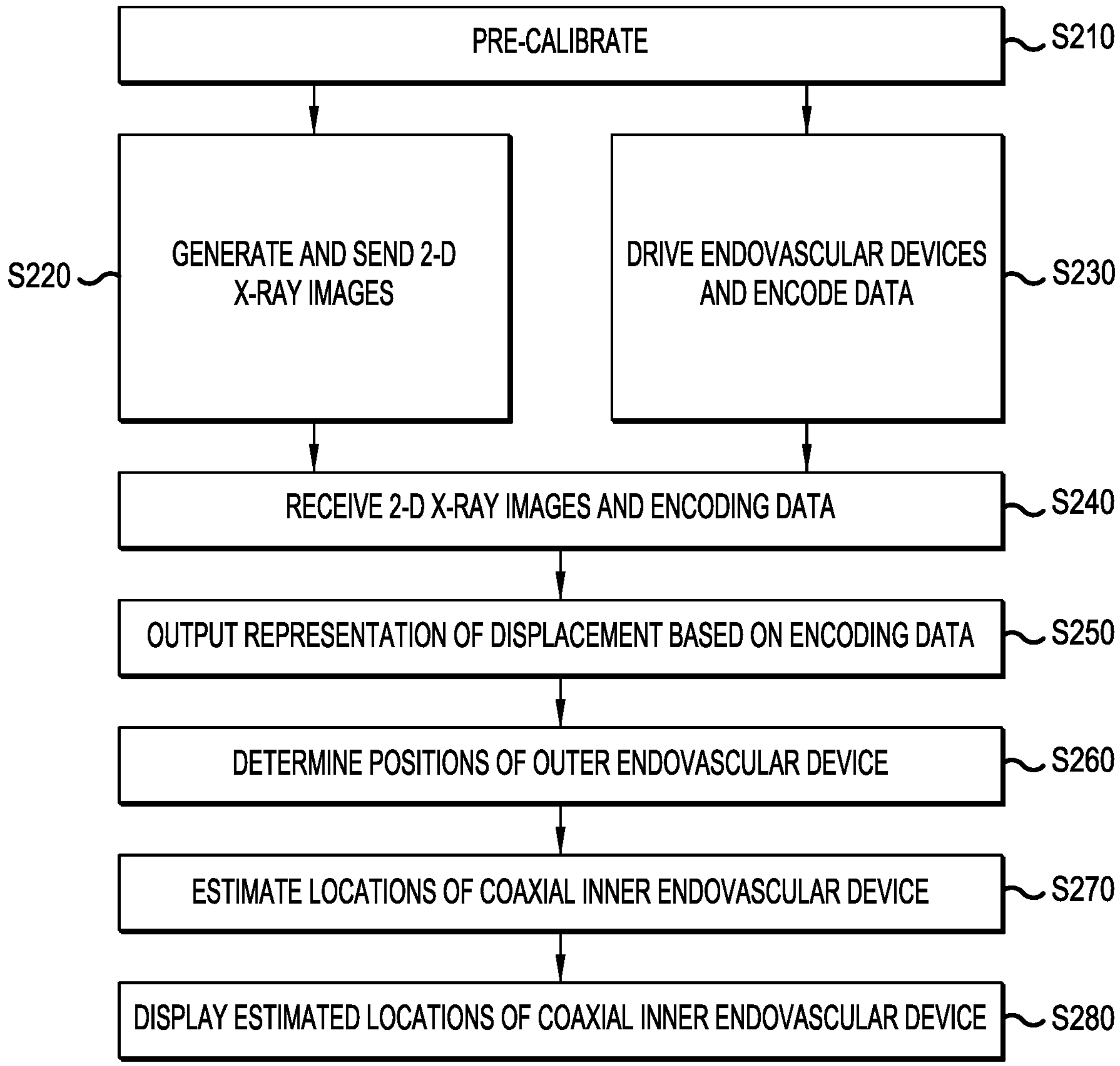
FIG. 2 illustrates a method for elongated device tracking, in accordance with a representative embodiment.

FIG. 2 illustrates a method for elongated device tracking, in accordance with a representative embodiment.

The method of FIG. 2 may be performed by the system 100 including the controller 150.

At S210, pre-calibration is performed. Pre-calibration may be performed based on timing a calibration of the encoding data when the tip of the guidewire as the inner device and the tip of the catheter as the outer device are aligned in the two-dimensional X-ray image. The association between encoding data and pixel position data along the catheter as the outer device may be based on the pre-calibration of the encoding data including determination of the encoding data when the two tips are aligned in the image.

The pre-calibration may be performed using the computer 110 and the display 180 in FIG. 1. For example, a user interface for the computer 110 may comprise a button that a user may press when the guidewire tip is believed to be at the end of the catheter based on the two-dimensional X-ray image currently displayed on the display 180. In some embodiments, the offset between the guidewire tip and the catheter tip may be calculated by the controller 150 when the user presses such a button based on the two-dimensional X-ray image currently displayed on the display 180. The button may comprise an interface such as a third interface configured to accept input to pre-calibrate a location of a tip of the outer elongated device and an estimated location of a tip of the inner elongated device.

In some embodiments, the controller 150 may automatically perform the calibration without a direct user instruction, such as based on interpreting the end of the catheter in the two-dimensional X-ray image on the display 180 and based on the encoding data for the guidewire from the encoder 145. The relative position of the tips (tip alignment) with respect to the encoder 145 may be calibrated whenever a new instance of the elongated device 120 is introduced. The robot 130 or another element of the system 100 may have specialized hardware for this. Alternatively, the X-ray image and image processing may be used to detect the event when the device tips are aligned in the image. The offset in the robot encoder space may then be noted. This may be accomplished by monitoring the guidewire protrusion length in pixels until the guidewire tip disappears in the catheter during guidewire retraction or catheter advancement or both simultaneously. Alternatively, the controller 150 may detect when the guidewire is first visible, during advancement out of the catheter, or when catheter is retracted.

At S220, two-dimensional X-ray images including image data are generated and sent. S220 may be performed repeatedly and in parallel with some or all of the steps from S230 to S270 in FIG. 2.

At S230, endovascular devices are driven and data corresponding to the driving of the endovascular devices is encoded. S230 may be performed repeatedly and in parallel with some S220 and all of the steps from S240 to S270 in FIG. 2.

At S240, the two-dimensional X-ray images and the encoding data are received. The two-dimensional X-ray images may be received at the computer 110 from the imaging device 101 via the first interface 111. The encoding data may be received at the computer 110 from the encoder 145 via the second interface 112.

At S250, a representation of displacement is output based on the encoding data. The representation may comprise an indication warning of the displacement or absence of the displacement of the guidewire relative to the displacement. The displacement may be an estimate of movement in one or more degrees of freedom of the elongated device 120 based on a number of rotations by the motor 140, based on the amount of time the motor 140 is driving the elongated device 120, based on a speed at which the motor 140 is driving the elongated device 120, and/or based on any other factors that may be taken into account by the encoder 145. The representation of displacement may be an amount of displacement in each of the one or more degrees of freedom.

At S260, positions of the outer endovascular device are determined. The controller 150 may calculate a set of order line segments representing the catheter of the elongated device 120 in the two-dimensional X-ray image. The positions determined at S260 may be determined based on an image analysis program implemented by the controller 150. An association between the encoding data received at S240 and positions of pixel data of the two-dimensional X-ray images received at S240 may be based on a pre-calibration.

At S270, locations of the coaxial inner endovascular device are determined. The locations of the coaxial inner endovascular device may involve several sub-processes starting with the encoding data from the encoder 145 to determine robot coordinates from absolute displacement of the guidewire based on movement by the robot 130 and then including calibration to the pixel coordinates to calculate the approximate distance in pixels from the tips of the devices, and then applying the approximate distance in pixels to the catheter line segments for the catheter to localize the tip of the guidewire on the image.

The determination at S270 may involve registering two or more coordinate systems to one another. For example, the robot 130 and the motor 140 may reference a first three-dimensional coordinate system, and the imaging device 101 may reference a second three-dimensional coordinate system. The two coordinate systems may be registered to one another to enable the translation of encoding data to the two-dimensional X-ray image in the three-dimensional coordinate system of the imaging device 101.

The determination at S270 may include applying a trained artificial intelligence model to the images and the encoding data to estimate the locations of the coaxial inner elongated device. In some embodiments, an association between encoding data from the encoder 145 and pixel position data along the outer device from image analysis performed by the controller 150 is based on the calibration of a scale factor between image and encoding data. The calibration may be performed at S210 as described above, and may include determination of the encoding data when the two tips are aligned in the image. The scale factor is constant over the entire image when the elongated device 120 is parallel with the detector plane from a two-dimensional X-ray detector, and otherwise the scale factor varies for each position of the catheter and guidewire of the elongated device 120.

An active calibration may be performed in relation to S270 but throughout most or all of an intervention so as to improve user experience and provide improved precision for the location of the guidewire tip inside the catheter. The active calibration may be performed to calibrate robot encoding data units from the encoder 145 to image units based on the two-dimensional X-ray imagery from the imaging device 101. An image analysis algorithm may detect the tip of the catheter in the two-dimensional X-ray image and provide a translation of the location of the catheter tip in the image. Corresponding location of the tip of the guidewire from motion of the guidewire may be determined from the encoding data from the encoder 145. A comparison yields a dimensional ratio that may then be applied to estimate location of the guidewire on the segmented representation of the catheter on the display 180. The pixel calibration algorithm may be run in real time and is described more below with respect to FIG. 4.

At S280, estimated locations of the coaxial inner endovascular device are displayed. When the guidewire tip of the elongated device 120 is retracted into the catheter of the elongated device 120, a highlight or other indicator may be generated and overlaid on the two-dimensional X-ray image at e.g. the location of the tip of the guidewire tip but on the display of the catheter of the elongated device 120 in the image. For example, the display 180 may output an indication that the guidewire as the inner elongated device is retracted entirely within the outer elongated device in image data of the images. The location of the guidewire tip is established at S270 based on the encoder values in the encoding data output by the encoder 145 at S240. The controller 150 may be configured to automatically estimate the locations of the inner elongated device once it is detected that the inner elongated device is retracted into the outer elongated device.

The display of the tip (or any other portion) of the guidewire at S280 may be performed at limited times during an intervention such as once the tip of the guidewire is fully retracted within the catheter, or may be performed throughout an intervention. In some embodiments, the controller 150 may selectively determine when to display the tip (or other portion) of the guidewire, such as based on proximity to the tip (or other portion) of the catheter, so as to display the tip of the guidewire even when the tip (or other portion) of the guidewire slightly extends from the catheter.

In some embodiments, the display of the tip of the guidewire may vary based on distance to the tip of the catheter. For example, the tip of the guidewire may be highlighted using variable sizes, shapes, and/or colors based on the distance to the tip. As an example, the highlight may change from blue to green going based on distance from tip alignment. As another example, the highlight may turn from a circular shape at the alignment location to progressively more oblong further away. The oblong shape may be used in embodiments where the calibration is relatively rough, and the oblong shape may cover potential regions where the tip is likely to be. In some embodiments, the overlays may vary based on the eigenvalues/eigenvectors of a system covariance matrix. In some embodiments, a circular highlight may change from small at alignment to larger diameter further from alignment.

Figure 3:
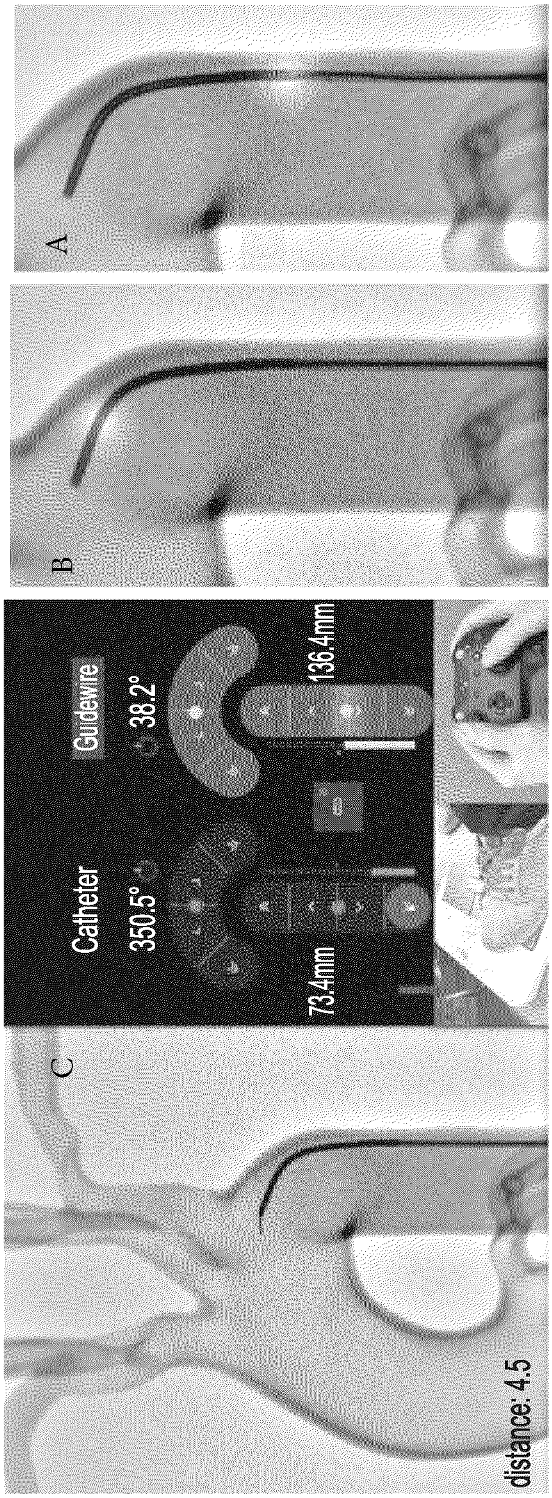
FIG. 3 illustrates user interfaces for elongated device tracking, in accordance with a representative embodiment.

FIG. 3 illustrates user interfaces for elongated device tracking, in accordance with a representative embodiment.

The user interfaces 381 in FIG. 3 illustrate aspects of an elongated device being imaged in anatomy. Visual cues are provided to a physician via the user interfaces 381 labelled as B and C. As a result, the physician may clearly monitor the location of the guidewire tip inside the catheter to avoid the errors. As shown, the tip location is highlighted.

In the first of the user interfaces 381 labelled as A, the guidewire is extended beyond the catheter as in normal. In the second and third of the user interfaces 381 labelled as B and C, the guidewire is retracted into the catheter with the estimated location of the tip of the guidewire highlighted by a highlighted visual overlay.

As an alternative (not shown), the user interface may include two or more (X-ray) two-dimensional images acquired from different view angles, acquired optionally simultaneously, showing therefore the anatomy and the catheter and/or guidewire from two or more different angles. One or more images may include the overlaid indicator of the tip (or other portion) of the guidewire according to this disclosure.

Figure 4:
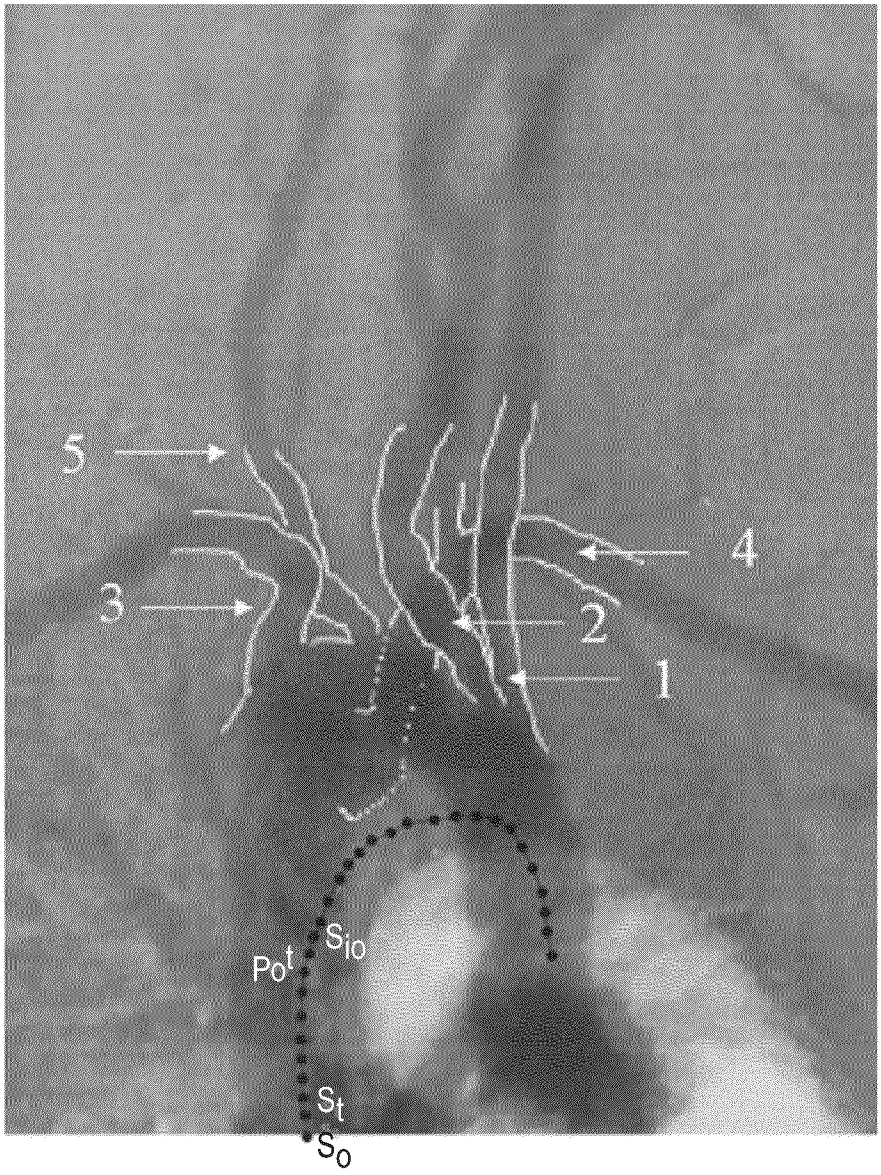
FIG. 4 illustrates an X-ray image for elongated device tracking, in accordance with a representative embodiment.

FIG. 4 illustrates an X-ray image for elongated device tracking, in accordance with a representative embodiment.

The user interface 481 in FIG. 4 illustrates an X-ray image with potential paths and locations for an elongated device in anatomy. In FIG. 4, the aortic arch and one endo-vascular device placed in the descending aorta are shown.

As described previously, an active calibration may be performed in relation to S270 in FIG. 2, but throughout most or all of an intervention. The active calibration may be performed to calibrate robot encoding data units from the encoder 145 to image units based on the two-dimensional X-ray imagery from the imaging device 101. An image analysis algorithm may detect the tip (or predetermined other portion) of the catheter in the two-dimensional X-ray image and provide a translation of the location of the catheter tip (or other predetermined portion) in the image. Corresponding location of the tip (or other predetermined portion) of the guidewire from motion of the guidewire may be determined from the encoding data from the encoder 145. A comparison yields a dimensional ratio that may then be applied to estimate location of the guidewire on the segmented representation of the catheter on the display 180.

Calibration of locations of the tip (or other predetermined portion) of the guidewire to a two-dimensional X-ray image involve two different complexities that are addressed by the controller 150. The first is that relative depth of the elongated device 120 varies for different positions of the elongated device 120 when the elongated device 120 is not entirely parallel to the imaging plane of the two-dimensional X-ray image. The second is that curvature and any bend in the catheter must be accounted for when determining translation of the guidewire within the catheter.

In FIG. 4, p0t is the tip of the catheter at time t. The catheter of the elongated device 120 may be described by a list of points p0t, p1t, . . . , pnt. Image-robot encoder scale factors along the centerline(s) of the vessels are shown as s0, s1, . . . , sk. Translational scale factors along centerlines of the outer elongated device may be assigned, wherein the translational scale factors provide variable translations between the encoding data and pixels. The scale factor provides the number of robot encoder counts per pixel, and this may vary based on the alignment of the elongated device 120 relative to the imaging plane, particularly in a two-dimensional image such as a two-dimensional X-ray image.

To compute image position of the tip of the guidewire, the catheter and guidewire tips are calibrated and the guidewire may be retracted with ct counts from the tip of the catheter. The controller 150 may count from the encoding data an amount of retraction of the inner elongated device relative to the tip of the outer elongated device. The position along the catheter trajectory corresponding to the tip of the guidewire is then found by a first algorithm. The first algorithm is for finding the guidewire tip, and involves first finding the centerline closest to the initial point in the list of points, and then adjusting based on the scale factor. The process may be performed for each point in the list of points, or for a limited set of points closest to an extremity designating the tip of the catheter. The vessel centerlines may be made available ahead of time. Alternatively, the vessel centerlines in the two-dimensional X-ray image may be computed dynamically while the catheter is inserted. The scale factors along the vessel center-axis can be computed iteratively through a second algorithm.

The second algorithm uses the displacement from the encoding data from the encoder 145, and updates the scale factor for each point in the list of points along the centerline of the catheter. The second algorithm is applied dynamically, depending on spatial and temporal parameters, and is used to create a mapping of the calibrations in at least the spatial domain for locations of calibrations on the image or in the vasculature.

The first algorithm may be run continuously during manipulation of the guidewire during an intervention. The scale factors corresponding to catheter points are initialized as soon as the tip passes through that region of the vasculature so the scale factors required to estimate the position of the guidewire inside the catheter are well defined. Several different schemes may be used to update the scale factors. For example, an advanced approach may take into consideration the direction and velocity of the encoder change, so as to improve the estimation insofar as the scale factor tends to be underestimated during a push due to buckling in the vasculature and overestimated during device pull due to slack removal.

In some embodiments, for either algorithm steps, the relative width of at least one elongated device in pixels may be used by the system to further or alternatively estimate scaling variation in the image. Especially if the actual width of said at least one device is known (e.g., in mm), it can be mapped to pixel width of the device in the image to estimate the scaling factor directly, or it can be used as supplemental information in the scaling factor algorithms.

In an additional or alternative embodiment, the device can also include opaque fiducials (i.e. opaque to imaging) of known size and/or known displacement on the elongated device, and the difference between the actual and imaged geometry of these fiducials can be used to estimate the scaling factor. In the case when the first scaling algorithm lacks sufficient information, the scaling factor can be derived directly from the image and the assumption that the device positioned in the iso-center of the imaging space, using standard projective geometry techniques.

In an additional or alternative embodiment, the system is arranged to estimate the orientation of the curvature of the outer device (that is curved) and to use this estimation to refine the scaling factor for the curved section to show the tip of the inner device in the correct visual location. An external system of estimating orientation of the curved device relative to the image is used to augment the information about the section of the device in the image. I.e., the relative position of distal sections of the curved device in and out of plane modulates the scaling factor. A particular section is moving away from the x-ray detector, it should have proportionally larger scaling factor (a given physical motion of the device will traverse more pixels in the image) than the scaling factor for sections of the device located relatively closer to the detector.

In case, when multi-plane x-ray imaging system (such as a biplane) is available, the scaling factor algorithm can be used in each image. The user interfaces can be applied to any of the image sources used in the algorithms, or can be automatically selected as the primary user interface based on the most accurate scaling factor, or availability of scaling factor, or user preference. In the case where the multi-plane x-ray imaging system is co-registered the device positions in the 3D space can be reconstructed using standard multi-view projective geometry methods. The scaling factor can be back calculated for the devices in the images.

In case when the action drive of the elongated devices is slipping, an occasional reset of the absolute position of devices can be done by referencing the event when the inner is visually detected in the image as entering or leaving the outer device tip.

The controller 150 may check if the guidewire is retracted based on the robot coordinates. When the guidewire is retracted, the scale factor may be applied to the encoder-based retraction distance to yield retraction length in pixels. This length is used to find a pixel location along the catheter line segments from the tip of the catheter, using Euclidian methods. At this location, a blending of a glyph/graphic with X-ray image pixels is performed to show estimated guidewire position as in FIG. 3.

FIG. 3 or 5 illustrates user interfaces for elongated device tracking, in accordance with a representative embodiment.

In some embodiments based on FIG. 3, the display of the tip of the guidewire may vary based on estimated relative position in-and-out of the image plane of the device tip inside the outer device. For example, the system is arranged such that color intensity is not the same when the inner device is moving away from or towards the viewer, or the size or shape of the display is changed based on how much it is out of plan, while traveling inside the outer device (do to forshortening). The relative in-and-out of plane of the device is directly proportional to the scaling factor.

Additional embodiments based on FIG. 3 can include an overlay graphic or contextual positioned at the location of functional information about the inner device, inside the outer device, such as a an articulation point or different stiffness region of the inner device, or device specific markers such as start and end of a stent, or balloon, or other diagnostic and treatment device information. The information can also be virtual, such as gradations indicating sections of the devices of equal length.

Figure 5B:
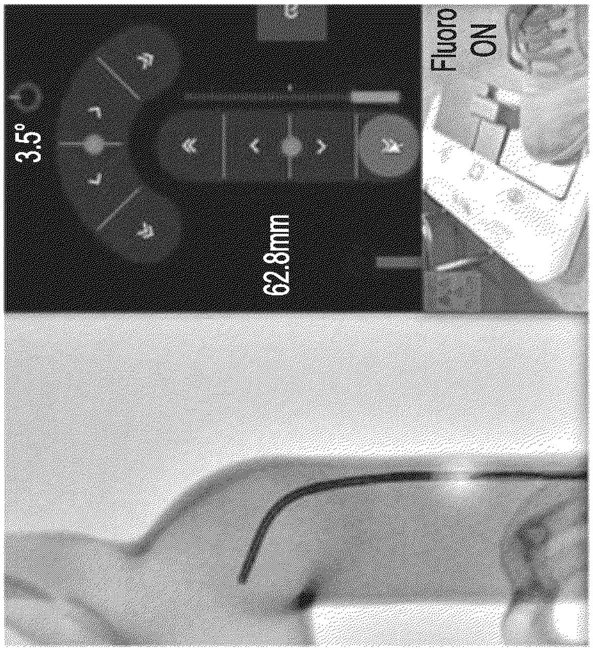
FIGS. 5A and 5B illustrates user interfaces for elongated device tracking, in accordance with a representative embodiment.
Figure 5A:
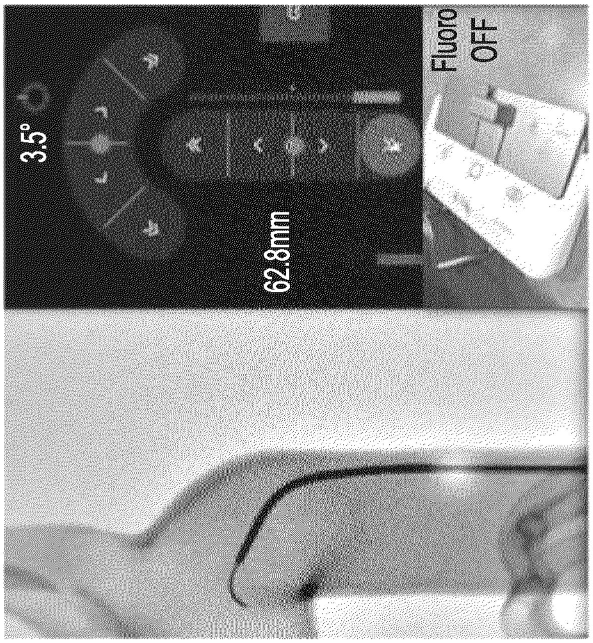

The user interfaces 581 in FIGS. 5A and 5B illustrate aspects of an elongated device being imaged in anatomy. In FIGS. 5A and 5B, location of the guidewire is overlaid on the most recent X-ray image even when the imaging device 101 is off as shown in the first of the user interfaces 581 labelled “A”. When a new acquisition is obtained, the overlay will render on the new image as shown on the second of the user interfaces 581 labelled “B”.

In embodiments based on FIGS. 5A and 5B, the controller 150 is used to estimate the location of the guidewire inside the catheter even when the X-ray is not enabled. The most recent X-ray image may be used for feedback, and the highlight may be drawn along the segmented device, as if the fluoroscopy was active. When the catheter is moved, as observed through the encoding data from the encoder 145, a warning may be displayed on the display 180, and/or another two-dimensional X-ray image may be taken to update the image.

In some embodiments similar to those based on FIGS. 5A and 5B, the fluoroscopy framerate may be reduced, such as by ½, when the guidewire is retracted into the catheter, and the updating to show estimated guidewire tip may be performed at the original frame rate.

Many variations are within the scope of the teachings above. For example, some elongated devices may include a catheter with some X-ray-transparent segments and some opaque segments, as shown in FIGS. 5A and 5B. In some embodiments, as the guidewire is advancing through the catheter in the X-ray-transparent segments, the guidewire tip may be detected in the two-dimensional X-ray image, and scale factors may be stored in a lookup table. When the guidewire enters the X-ray-opaque segment, linear the scale factor may be dynamically updated based on the lookup table parameters.

In some embodiments, more than one endovascular devices may be tracked using the system 100 and the method of FIG. 2. For example, stents, a balloon and other types of endovascular devices may be tracked within a catheter as the elongated device 120, using the teachings herein.

In some embodiments, the robot motion will be augmented depending on the relative position of each device to the tip. For example, in the case when the inner device is inside the outer device and is approaching the tip of the outer device, its speed is limited to a preset value at a particular distance, or a continuous function based on the distance to the tip. The speed limit can be based on the direction of motion of the inner device inside the outer device, for example, retraction into the outer device has a higher speed limit, than the advancement towards the tip of the outer device.

FIG. 6 illustrates a computer system, on which a method for elongated device tracking is implemented, in accordance with another representative embodiment.

Referring to FIG. 6, the computer system 600 includes a set of software instructions that can be executed to cause the computer system 600 to perform any of the methods or computer-based functions disclosed herein. The computer system 600 may operate as a standalone device or may be connected, for example, using a network 601, to other computer systems or peripheral devices. In embodiments, a computer system 600 performs logical processing based on digital signals received via an analog-to-digital converter.

In a networked deployment, the computer system 600 operates in the capacity of a server or as a client user computer in a server-client user network environment, or as a peer computer system in a peer-to-peer (or distributed) network environment. The computer system 600 can also be implemented as or incorporated into various devices, such as a workstation that includes a controller, a stationary computer, a mobile computer, a personal computer (PC), a laptop computer, a tablet computer, or any other machine capable of executing a set of software instructions (sequential or otherwise) that specify actions to be taken by that machine. The computer system 600 can be incorporated as or in a device that in turn is in an integrated system that includes additional devices. In an embodiment, the computer system 600 can be implemented using electronic devices that provide voice, video or data communication. Further, while the computer system 600 is illustrated in the singular, the term "system" shall also be taken to include any collection of systems or sub-systems that individually or jointly execute a set, or multiple sets, of software instructions to perform one or more computer functions.

As illustrated in FIG. 6, the computer system 600 includes a processor 610. The processor 610 may be considered a representative example of a processor of a controller and executes instructions to implement some or all aspects of methods and processes described herein. The processor 610 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 610 is an article of manufacture and/or a machine component. The processor 610 is configured to execute software instructions to perform functions as described in the various embodiments herein. The processor 610 may be a general-purpose processor or may be part of an application specific integrated circuit (ASIC). The processor 610 may also be a microprocessor, a microcomputer, a processor chip, a controller, a microcontroller, a digital signal processor (DSP), a state machine, or a programmable logic device. The processor 610 may also be a logical circuit, including a programmable gate array (PGA), such as a field programmable gate array (FPGA), or another type of circuit that includes discrete gate and/or transistor logic. The processor 610 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 600 further includes a main memory 620 and a static memory 630, where memories in the computer system 600 communicate with each other and the processor 610 via a bus 608. Either or both of the main memory 620 and the static memory 630 may be considered representative examples of a memory of a controller, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 620 and the static memory 630 are articles of manufacture and/or machine components. The main memory 620 and the static memory 630 are computer-readable mediums from which data and executable software instructions can be read by a computer (e.g., the processor 610). Each of the main memory 620 and the static memory 630 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 600 further includes a video display unit 650, such as a liquid crystal display (LCD), an organic light emitting diode (OLED), a flat panel display, a solid-state display, or a cathode ray tube (CRT), for example. Additionally, the computer system 600 includes an input device 660, such as a keyboard/virtual keyboard or touch-sensitive input screen or speech input with speech recognition, and a cursor control device 670, such as a mouse or touch-sensitive input screen or pad. The computer system 600 also optionally includes a disk drive unit 680, a signal generation device 690, such as a speaker or remote control, and/or a network interface device 640.

In an embodiment, as depicted in FIG. 6, the disk drive unit 680 includes a computer-readable medium 682 in which one or more sets of software instructions 684 (software) are embedded. The sets of software instructions 684 are read from the computer-readable medium 682 to be executed by the processor 610. Further, the software instructions 684, when executed by the processor 610, perform one or more steps of the methods and processes as described herein. In an embodiment, the software instructions 684 reside all or in part within the main memory 620, the static memory 630 and/or the processor 610 during execution by the computer system 600. Further, the computer-readable medium 682 may include software instructions 684 or receive and execute software instructions 684 responsive to a propagated signal, so that a device connected to a network 601 communicates voice, video or data over the network 601. The software instructions 684 may be transmitted or received over the network 601 via the network interface device 640.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, elongated device tracking enables incorporation of visual cues on a fluoroscopy image so that a physician may clearly monitor the location of the guidewire tip inside the catheter.

In this disclosure, some examples were based on locations of "tip" of the inner device (and/or of the outer device). Now the invention includes also locations of other predetermined portions of the inner device (and/or of the outer device) as long as these predetermined portions are initially well-defined (e.g. with respect to known portions or tips of the inner device and/or outer device).

Although elongated device tracking has been described with reference to several exemplary embodiments, it is understood that the words that have been used are words of description and illustration, rather than words of limitation. Changes may be made within the purview of the appended claims, as presently stated and as amended, without departing from the scope and spirit of elongated device tracking in its aspects. Although elongated device tracking has been described with reference to particular means, materials and embodiments, elongated device tracking is not intended to be limited to the particulars disclosed; rather elongated device tracking extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true scope of the present disclosure. Thus, to the maximum extent allowed by law, the scope of the present disclosure is to be determined by the broadest permissible interpretation of the following claims and shall not be restricted or limited by the foregoing detailed description.

The invention claimed is:

1. A system for tracking coaxial elongated devices in an anatomy, wherein the coaxial elongated devices comprise an outer elongated device and an inner elongated device driven by a motor, comprising a computer comprising:
- a controller;
- a first interface configured to receive images including at least one of the outer elongated device and the inner elongated device; and
- a second interface configured to receive encoding data representative of driving of the inner elongated device by the motor,
- wherein the controller is configured to:
  - receive via the first interface images including at least one of the outer elongated device, the inner elongated device being retracted within the outer elongated device;
  - receive via the second interface the encoding data;
  - determine positions of the outer elongated device; and
  - estimate locations of the inner elongated device retracted within the outer elongated device based on the positions of the outer elongated device and the encoding data.

2. The system of claim 1,
- wherein the controller is further configured to:
- provide display information such that a display can show estimated locations of the inner elongated device superimposed on the outer elongated device,
- wherein the inner elongated device is at least partially hidden within the outer elongated device.

3. The system of claim 2, wherein the estimated locations include estimated locations of a tip of the inner elongated device.

4. The system of claim 1, wherein the images comprise two-dimensional X-ray images, and
- wherein the coaxial elongated devices comprise an endovascular device.

5. The system of claim 1, wherein an association between the encoding data and positions of pixel data of the images is based on a pre-calibration.

6. The system of claim 5, further comprising:
- a third interface configured to accept input to pre-calibrate a location of a tip of the outer elongated device and an estimated location of a tip of the inner elongated device.

7. The system of claim 1, wherein the controller is further configured to:
- control motion of at least one of the outer elongated device and the inner elongated device.

8. The system of claim 1, wherein the locations of the inner elongated device are estimated only when the inner elongated device is retracted into the outer elongated device.

9. The system of claim 1, wherein the controller is further configured to:
- calculate approximate distances in pixels from a tip of the outer elongated device to a tip of the inner elongated device.

10. The system of claim 1, wherein the controller is further configured to:
- actively calibrate the encoding data to pixel data of the images.

11. The system of claim 1, wherein the controller is further configured to:
- identify locations of a tip of the outer elongated device in image data of the images;
- assign translational scale factors along centerlines of the outer elongated device, wherein the translational scale factors provide variable translations between the encoding data and pixels;
- count from the encoding data an amount of retraction of the inner elongated device relative to the tip of the outer elongated device; and
- identify a position along a trajectory of the outer elongated device corresponding to a tip of the inner elongated device.

12. The system of claim 1, wherein the controller is further configured to:
- output an indication that the inner elongated device is retracted entirely within the outer elongated device in image data of the images.

13. The system of claim 12, wherein the controller is further configured to:
- detect when the inner elongated device is being retracted entirely within the outer elongated device in image data of the images, and
- automatically estimate the locations of the inner elongated device once it is detected that the inner elongated device is retracted into the outer elongated device.

14. The system of claim 1, wherein the controller is further configured to:
- estimate locations of at least one additional elongated device within the outer elongated device.

15. The system of claim 1, further comprising:
- at least one of: the motor providing encoding data to the second interface; a robotic system comprising the motor and a processor to control at least one of the coaxial elongated devices; an imaging device to provide the images to the first interface; the inner elongated device; or the outer elongated device.

16. A controller for tracking coaxial elongated devices in an anatomy, comprising:
- a memory that stores instructions;
- a processor that executes the instructions;
- a first interface configured to receive images including an outer elongated device with a coaxial inner elongated device driven by a motor;
- a second interface configured to receive encoding data corresponding to driving of the coaxial inner elongated device by the motor, wherein, when executed by the processor, the instructions cause a system which includes the controller to:

receive the images including at least one of the outer elongated device and the coaxial inner elongated device;

receive the encoding data;

determine positions of the outer elongated device; and estimate locations of the coaxial inner elongated device retracted within the outer elongated device based on the positions of the outer elongated device and the encoding data.

17. The controller of claim 16, wherein, when executed by the processor, the instructions further cause the controller to:

provide, to a display, data for the estimated locations of the coaxial inner elongated device superimposed on the outer elongated device, wherein the coaxial inner elongated device is at least partially hidden within the outer elongated device.

18. The controller of claim 16, wherein, when executed by the processor, the instructions further cause the controller to:

apply a trained artificial intelligence model to the images and the encoding data to estimate the locations of the coaxial inner elongated device.

19. A method for tracking coaxial elongated devices in an anatomy, comprising:

receiving, via a first interface, images including at least one of an outer elongated device or a coaxial inner elongated device driven by a motor;

receiving, via a second interface, encoding data corresponding to driving of the coaxial inner elongated device by the motor;

determining positions of the outer elongated device; and estimating locations of the coaxial inner elongated device retracted within the outer elongated device based on the positions of the outer elongated device and the encoding data.

20. The method of claim 19, further comprising:

displaying, on a display, estimated locations of the coaxial inner elongated device superimposed on the outer elongated device, wherein the coaxial inner elongated device is at least partially hidden within the outer elongated device.

21. The method of claim 19, wherein the estimated locations include estimated locations of a tip of the coaxial inner elongated device.

22. The method of claim 21, wherein the images comprise two-dimensional X-ray images, and wherein the elongated device comprises an endovascular device.

* * * * *